(12) United States Patent
Löwel et al.

(10) Patent No.: US 7,175,979 B2
(45) Date of Patent: Feb. 13, 2007

(54) PRESERVED TISSUE MATRIX OF A HOLLOW ORGAN, PARTICULARLY OF A BLOOD VESSEL, A METHOD OF PRODUCING SAME, AND THE USE THEREOF

(75) Inventors: Matthias Löwel, Nürnberg (DE); Vilma Siodla, Kleinmachnow (DE)

(73) Assignee: Co. Don AG, Teltow (DE)

( * ) Notice: Subject to any disclaimer, the term of this patent is extended or adjusted under 35 U.S.C. 154(b) by 470 days.

(21) Appl. No.: 10/414,942

(22) Filed: Apr. 16, 2003

(65) Prior Publication Data

US 2004/0029095 A1    Feb. 12, 2004

(30) Foreign Application Priority Data

Apr. 18, 2002   (DE) ............................... 102 17 779

(51) Int. Cl.
 *A01N 1/00* (2006.01)
 *A61F 2/06* (2006.01)
 *A61F 2/04* (2006.01)
(52) U.S. Cl. ........................... 435/1.1; 623/1.1; 600/36
(58) Field of Classification Search ................ None
See application file for complete search history.

(56) References Cited

U.S. PATENT DOCUMENTS 4,098,571 A * 7/1978 Miyata et al. .............. 422/100
6,743,574 B1 * 6/2004 Wolfinbarger et al. ....... 435/1.1

FOREIGN PATENT DOCUMENTS

| DE | 2 004 553 | 5/1971 |
| DE | 29 06 650 A1 | 8/1980 |
| DE | 38 35 237 C1 | 12/1989 |
| DE | 198 28 726 A1 | 1/1999 |
| WO | WO 98/49969 | 11/1998 |
| WO | WO 99/00152 | 1/1999 |

* cited by examiner

*Primary Examiner*—Sandra E. Saucier
(74) *Attorney, Agent, or Firm*—Norris McLaughlin & Marcus PA

(57) ABSTRACT

The invention relates to a preserved, deantigenated tissue matrix of an animal or human hollow organ, e.g. of a blood vessel, of the ureter or urinary bladder, which matrix is autologous, allogenic or xenogenic with respect to a recipient and whose biomechanical properties are not or only slightly impaired by such preservation, which does not include any infectious particles from the donor and is excellently suited for coating with recipient endothelial, epithelial, fibroblast, or muscle cells in order to produce autologous grafts for said recipient. The invention is also directed to a method of producing said tissue matrix and to the use thereof, as well as to the autologous graft produced therefrom, and to the production and use thereof.

12 Claims, No Drawings

PRESERVED TISSUE MATRIX OF A HOLLOW ORGAN, PARTICULARLY OF A BLOOD VESSEL, A METHOD OF PRODUCING SAME, AND THE USE THEREOF

The invention relates to a preserved, deantigenated tissue matrix of an animal or human hollow organ, e.g. of a blood vessel, of the ureter or urinary bladder, which matrix is autologous, allogenic or xenogenic with respect to a recipient and whose biomechanical properties are not or only slightly impaired by such preservation, which does not include any infectious particles from the donor and is excellently suited for coating with recipient endothelial, epithelial, fibroblast, or muscle cells in order to produce autologous grafts for said recipient. The invention is also directed to a method of producing said tissue matrix and to the use thereof, as well as to the autologous graft produced therefrom, and to the production and use thereof.

In the course of operations on hollow organs of the blood vessel, lymphatic, respiratory and urogenital systems, there is frequently a need of replacing affected endogenous tissue and organ structures.

Where sufficient replacement tissue of a patient (autologous tissue) is available, as is the case e.g. in coronary bypass surgery, the attending physician will preferably transplant the autologous tissue.

Where autologous tissue is not sufficiently available, the physician has the following options:
- use of so-called biocompatible synthetic implants which may be both absorbable and non-absorbable;
- use of allogenic grafts, e.g. cardiac valves, blood vessels;
- use of xenogenic grafts, e.g. cardiac valves.

The use of synthetic implants sometimes involves severe side effects such as foreign body reactions, allergic reactions, lacking remodeling behavior, and also, life-threatening side effects such as thromboses. For this reason, their use in e.g. vascular and cardiac surgery is only possible in exceptional cases.

Apart from possible risks of infection, the use of allogenic vital grafts is limited due to graft rejection.

Allogenic non-vital grafts (produced e.g. by cryopreservation) have been used successfully for a long time in replacing affected bone and connective tissue structures (e.g. duraplasty, hernia operations).

However, their use in replacing tissue or organ structures assuming important metabolic functions, such as blood vessels, is limited. Lacking metabolic activity of the blood vessel walls gives rise to complications such as thromboses.

Non-vital xenogenic grafts, such as chemically modified cardiac valves of pigs, have been used successfully in cardiac surgery for a long time. However, they also involve some drawbacks such as calcification and lacking remodeling.

It is an object of the invention to provide a preserved tissue matrix of a hollow organ, whose biomechanical properties are largely the same as those prior to preservation, which is deantigenated, does not include any infectious particles from the donor, and is suitable for coating with recipient endothelial, epithelial, fibroblast, or muscle cells in order to be used in the production of autologous grafts for said recipient.

Another object of the invention is to devise a low-cost method of producing autologous grafts which can be used in abdominal, thoracic, vascular or cardiac surgery, in urology or gynecology.

The object of the invention is accomplished by means of a method for the production of a preserved tissue matrix of a hollow organ, which method is characterized in that a hollow organ tissue matrix collected from a human or animal body, subsequent to optional mechanical removal of adherent supporting, connective or fat tissue, is subjected to an osmotic treatment by repeated washings with aqueous salt solutions, the tissue matrix is deantigenated by repeated washings with aqueous hydrogen peroxide solutions, the matrix is subsequently treated with an alkaline solution and neutralized, the water present in the matrix is removed azeotropically by repeated washings with an organic, water-miscible solvent, and the matrix, now including solvent, is dried.

In the meaning of the invention, said tissue matrix of a hollow organ is understood to be a preferably tubular piece of tissue of a blood vessel, e.g. a piece of an artery, vein or of a lymphatic vessel. According to the invention, however, it is also possible to use ureters, urinary bladders, tracheae, bronchial tubes, tissues of stomach and intestinal walls. The invention relates to all those tissues assuming an important metabolic function, such as blood vessels, and those including both collagen and elastin, as well as muscle cells.

According to the invention, the collected tissue—optionally after previous removal of adherent supporting, connective or fat tissue—is washed repeatedly with aqueous salt solutions and optionally stored therein overnight in order to destroy the donor cells included in the matrix by osmosis. 5–15% salt solutions are used to this end. Sodium chloride, sodium phosphate, sodium sulfate, sodium hydrogen phosphate, sodium hydrogen sulfate, sodium citrate are possible as salts. It is preferred to use sodium chloride.

This is followed by deantigenation effected by washing with aqueous hydrogen peroxide solutions. This is followed by optional storage in an $H_2O_2$ solution which preferably is 3–10%. It has been determined that the use of $H_2O_2$ results in a reduction of the DNA content in the tissue matrix by up to 50%.

According to the invention, the tissue matrix is subsequently treated with an alkaline solution, preferably with NAOH or KOH. It is preferred to use a 0.1–1 N alkaline solution. Depending on the concentration of the alkaline solution, it has been found that it is possible to achieve a reduction of the genuine DNA content in the tissue matrix by up to 80% (with a 0.1 N alkaline solution) or up to 100% when using a 1 N alkaline solution.

In the last step, following neutralization, the matrix is subjected to mild drying by azeotropic removal of water from the matrix, which is done by repeated washing with an organic, water-miscible solvent, e.g. ethanol, methanol, propanol, acetone. According to the invention, the use of ethanol is preferred. This step of solvent preservation of tissue is a well-known method described e.g. in DE 29 06 650.

The combined use of $H_2O_2$ and alkaline solution in the course of tissue matrix preservation achieves decellularization of the matrix and complete elimination of matrix DNA and infectious particles. In particular, the method of tissue preservation according to the invention provides a matrix wherein biomechanical stability and tissue structure remain largely unchanged after rehydration, so that a graft produced using said matrix has good in vivo tissue compatibility and undergoes partial or complete remodeling inside the body, i.e., is transformed into autologous tissue.

One particular advantage of the tissue matrix produced according to the invention is that colonization with autologous cells can proceed in such a way that in some or all of the cases the use of components promoting cell adherence, such as fibrin, fibrinogen or autologous serum, is not required. This dramatically reduces the cost and greatly simplifies the production of autologous grafts. Moreover, collecting autologous serum is problematic in some cases, e.g. in heart patients, because large volumes of blood must be withdrawn from these per se weakened patients in order to collect the serum.

Apart from the preserved tissue matrix produced according to the invention, the invention is also directed to the use thereof in the production of a graft autologous with respect to the recipient by rehydration of the matrix and colonization thereof by recipient-specific cells, wherein several different types of cells can be used, e.g. endothelial, epithelial and/or muscle cells to coat a blood vessel, e.g. muscle cells and endothelial cells. It is possible to combine multiple types of cells lying one on top of the other. However, if multiple layers of cells are to be coated, previous coating of the matrix with agents promoting cell adherence is recommended, the amount required being low owing to the way of matrix preservation.

The autologous cells required for colonization (of the tissue matrix produced according to the invention, which is allogenic or xenogenic with respect to the recipient) are collected from tissue biopsy material having structural and metabolic properties identical or similar to those of the tissue structure to be replaced. The cells obtained after disintegration of the tissue are cultured in a well-known manner.

Expansion of the cells to a number corresponding to the respective area to be colonized is effected using appropriate cell-specific culturing media, with optional addition of autologous serum.

Prior to colonization, the preserved tissue matrix is rehydrated, preferably using isotonic buffer solutions, and subsequently fixed in a suitable apparatus for colonization, if necessary. Thereafter, uniform coating of the rehydrated tissue matrix can be performed using an agent promoting cell adherence. According to the invention, however, said coating is omitted. For coating, the tissue matrix is subsequently incubated with a cell suspension including a well-defined number of autologous cells, said incubation being effected repeatedly, if necessary. Thereafter, cell culturing required to achieve a completely coated surface is effected in specific cell culture media. After completion of cell culturing, the graft is washed with isotonic buffer solutions and subsequently packed in an isotonic salt solution to be ready for dispatch.

Owing to the advantageous properties of the tissue matrix employed, the grafts produced according to the invention, which also represent a subject matter of the present invention, are excellently suited for use in abdominal, thoracic, vascular or cardiac surgery, in urology or gynecology.

Thus, in the event of a gastric tumor, for example, the affected area can be replaced with a xenogenic patch colonized with muscle and mucosa cells.

In tracheal partial resections, for example, the affected section can be replaced with a xenogenic trachea colonized with autologous epithelial cells.

Bypass operations in the peripheral and aortocoronary regions can be performed using grafts consisting of allogenic vascular matrices colonized with autologous endothelial cells.

In urinary bladder resection, a preserved hollow organ of allogenic or xenogenic origin equal in size and colonized with autologous epithelial cells can be transplanted as a substitute.

According to the invention, it is also possible to produce a patch from a preserved hollow organ tissue matrix by axially dissecting the hollow organ, e.g. blood vessel. Following rehydration, this piece of tissue, now being flat and colonized with cells or not, can be used as a flat cover on defects in a human or animal body.

For example, this is the case in the removal of cerebral tumors and subsequent duraplasty using a patch not colonized with cells.

Also, treatment of urinary incontinence using non-colonized patches in a sling procedure is possible.

In this latter case, these patches optionally can be colonized with autologous fibroblasts so as to achieve more rapid tissue integration.

EXAMPLE

The following example exemplifies the production of a coronary blood vessel consisting of a xenogenic matrix and coated with autologous endothelial cells.

a) A vein about 15 cm in length and with an inner diameter of about 4 mm is prepared from the muscular mass of a pig and subsequently made free of adherent connective tissue by hand. Thereafter, the lumen is washed repeatedly with a saline solution until complete removal of blood is achieved. This is subsequently washed with salt solutions so as to destroy the cells included in the matrix by osmosis. This is followed by deantigenation with hydrogen peroxide solutions. Thereafter, this is treated with 0.1 N NaOH for one hour, followed by neutralization with acetic acid for 15 minutes and washing with purified water.

Azeotropic removal of water from the matrix thus obtained is effected by repeated washing with ethanol.

The matrix thus treated is dried to a content of 50 ppm ethanol at maximum and subsequently packed in a double-sterile fashion. Final sterilization can be effected with gamma rays at a dose of 25 kGy, for example.

b) The autologous endothelial cells are collected from a suitable vein of the patient. Included blood components are removed by repeated washing of the lumen with phosphate buffer solution. Thereafter, the lumen of the vein is incubated with collagenase P for about 20 minutes at 37° C. The wash solution thus obtained is centrifuged, the supernatant is discarded, and the resulting cell pellet is resuspended in a cell culture medium suitable for endothelial cells, e.g. Endomed®. Subsequently, this cell suspension is seeded into a 25 $cm^2$ cell culture flask.

c) The endothelial cells are cultured for about 24 days at 37° C., 95% r.h. and 5% $CO_2$.

This includes two passages wherein transference into 75 $cm^2$ and subsequently into 225 $cm^2$ cell culture flasks is effected.

d) The preserved pig vein is placed in an insulator through a gate and rehydrated with 0.9% NaCl solution under aseptic conditions. (Subsequently, the inner surface of the pig vein can be coated with fibrin glue or autologous serum. Smoothing of the fibrin glue or serum layer can be effected using a Fogarty catheter.)

Subsequently, the pig vein thus pretreated is washed with 0.9% NaCl solution. Thereafter, the lumen is filled with Endomed® endothelial cell medium having a well-defined number of endothelial cells suspended therein. Both ends of the vein are sealed by means of spring clamps. Now, the matrix thus treated is placed in a Petri dish filled with Endomed® medium and incubated for about 45–75 minutes.

Subsequently, this is transferred into a cell culture flask and cultured at 37° C. for 5–9 days, leaving the medium unchanged.

e) After complete colonization of the pig vein with endothelial cells, the Endomed® medium is removed, the pig vein is washed with sterile phosphate buffer and subsequently filled with 0.9% NaCl solution.

Shipping to physicians is effected in sterile packages in 0.9% NaCl solution at 2–8° C. using a refrigerated distribution chain.

The invention claimed is:

1. A method for the production of a preserved tissue matrix of a hollow organ comprising
   collecting a hollow organ tissue matrix from a human or animal body,
   optionally mechanically removing adherent supporting, connective or fat tissue,
   subjecting the tissue matrix to an osmotic treatment by repeatedly washing with an aqueous salt solutions,
   deantigenating the tissue matrix by repeatedly washing with an aqueous hydrogen peroxide solutions,
   treating the tissue matrix with an alkaline solution
   neutralizing the pH of the tissue,
   removing the water from the tissue matrix azeotropically by repeatedly washing the tissue matrix with an organic, water-miscible solvent, and
   drying the tissue matrix, thereby producing a preserved tissue matrix of a hollow organ.

2. The method according to claim 1,
   wherein
   5 to 15% solutions are used as salt solutions in the osmotic treatment.

3. The method according to claim 1,
   wherein
   the aqueous hydrogen peroxide solution is 3–10% $H_2O_2$ solution.

4. The method according to claim 1,
   wherein
   the alkaline solution is 0.1–1 N alkaline solution.

5. The method according to claim 1,
   wherein
   the organic, water-miscible solvent is ethanol.

6. The method according to claim 1,
   wherein
   the hollow tissue matrix is a blood vessel.

7. The method according to claim 1,
   further comprising
   dissecting axially the preserved tissue to produce a patch.

8. A preserved tissue matrix of a hollow organ, produced according to claim 1.

9. A method for covering defects in a human or animal body, comprising the step of applying a patch produced according to claim 7.

10. The method according to claim 1,
    wherein
    the salt solution is 5 to 15% NaCl.

11. The method according to claim 1,
    wherein
    the hollow tissue matrix is an artery or vein.

12. The method according to claim 1,
    wherein
    the alkaline solution is 0.1–1 N NaOH or KOH.

* * * * *